(12) United States Patent
Kawata et al.

(10) Patent No.: US 11,076,831 B2
(45) Date of Patent: Aug. 3, 2021

(54) ULTRASOUND DIAGNOSIS APPARATUS, SIGNAL PROCESSING APPARATUS, AND SIGNAL PROCESSING METHOD

(71) Applicant: Toshiba Medical Systems Corporation, Otawara (JP)

(72) Inventors: Satoshi Kawata, Yokohama (JP); Toshiyuki Ono, Kawasaki (JP); Toshimitsu Kaneko, Kawasaki (JP); Tomoyuki Takeguchi, Kawasaki (JP); Ryota Osumi, Nasushiobara (JP); Tomohisa Imamura, Kawasaki (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 457 days.

(21) Appl. No.: 15/443,126

(22) Filed: Feb. 27, 2017

(65) Prior Publication Data
US 2017/0245832 A1    Aug. 31, 2017

(30) Foreign Application Priority Data

Feb. 29, 2016 (JP) .............................. JP2016-038009

(51) Int. Cl.
*A61B 8/08*    (2006.01)
*A61B 8/06*    (2006.01)

(52) U.S. Cl.
CPC .............. *A61B 8/5207* (2013.01); *A61B 8/06* (2013.01); *A61B 8/485* (2013.01); *A61B 8/488* (2013.01)

(58) Field of Classification Search
CPC ......... A61B 8/5207; A61B 8/485; A61B 8/06; A61B 8/488
See application file for complete search history.

(56) References Cited

U.S. PATENT DOCUMENTS 5,228,009 A * 7/1993 Forestieri ................ G01S 15/58
                                                        367/11
5,299,174 A * 3/1994 Forestieri ................ G01S 15/58
                                                        367/11
(Continued)

FOREIGN PATENT DOCUMENTS

JP        4369427        11/2009

OTHER PUBLICATIONS

Lasse Lovstakken, Signal Processing in Diagnostic Ultrasound: Algorithms for real-time estimation and visualization of blood flow velocity, Feb. 2007, Department of Circulation and Medical Imaging (Year: 2007).*

(Continued)

*Primary Examiner* — Hien N Nguyen
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry obtains time-series data having complex values based on a reflected wave of an ultrasound wave transmitted by an ultrasound probe and calculates an expansion coefficient in a case in which the obtained time-series data is expressed as a linear sum of a plurality of mathematical functions, the time-series data having, as an argument, a first parameter related to time. The plurality of mathematical functions are mathematical functions that are possible to be generated on a basis of a function family that has, as arguments, the first parameter and a second parameter different from the first parameter.

17 Claims, 9 Drawing Sheets

(56) References Cited

U.S. PATENT DOCUMENTS

| | | | | |
|---|---|---|---|---|
| 5,349,524 A * | 9/1994 | Daft | ............... | G01S 7/52071 367/135 |
| 5,413,105 A * | 5/1995 | Forestieri | ............ | G01S 7/52028 600/441 |
| 5,913,824 A * | 6/1999 | Ogasawara | ......... | G01S 15/8981 600/455 |
| 7,942,821 B2 | 5/2011 | Umemura et al. | | |
| 2007/0167791 A1 * | 7/2007 | Umemura | ........... | G01S 15/8977 600/455 |
| 2011/0313292 A1 * | 12/2011 | Kwak | .................. | A61B 8/06 600/453 |
| 2015/0150535 A1 * | 6/2015 | Fan | ...................... | A61B 8/485 600/438 |

OTHER PUBLICATIONS

Evans et al., Ultrasonic colour Doppler imaging, May 6, 2011 (Year: 2011).*

Dahl et al., Reverberation Clutter from Subcutaneous Tissue Layers: Simulation and in vivo Demonstrations, Apr. 2014 (Year: 2014).*

Anthony P. Kadi, et al., "On the Performance of Regression and Step-Initialized IIR Clutter Filters for Color Doppler Systems in Diagnostic Medical Ultrasound", IEEE Transactions on Ultrasonics, Ferroelectrics, and Frequency Control, vol. 42, (5) 1995, 11 pgs.

* cited by examiner

ULTRASOUND DIAGNOSIS APPARATUS, SIGNAL PROCESSING APPARATUS, AND SIGNAL PROCESSING METHOD

CROSS-REFERENCE TO RELATED APPLICATIONS

This application is based upon and claims the benefit of priority from Japanese Patent Application No. 2016-038009, filed on Feb. 29, 2016; the entire contents of which are incorporated herein by reference.

FIELD

Embodiments described herein relate generally to an ultrasound diagnosis apparatus, a signal processing apparatus, and a signal processing method.

BACKGROUND

Examples of modes used in ultrasound diagnosis processes performed by ultrasound diagnosis apparatuses include a Doppler mode. In the Doppler mode, an ultrasound probe emits an ultrasound wave multiple times in mutually the same direction toward a site subject to observation (hereinafter, "observation target") that is moving at predetermined velocity, so that the velocity of a blood flow component, for example, is calculated by detecting a frequency shift (a Doppler change) caused by a Doppler effect.

Mixed with a signal of the blood flow component serving as the observation target, reception signals in the Doppler mode include a signal called a clutter component, which originates from tissues that are either stationary or moving at low velocity. Usually, the signal intensity of the clutter component is higher than the signal intensity of the blood flow component, by tens to hundreds of decibels (dB). For this reason, the clutter component is eliminated to extract the signal of the blood flow component.

As a method for eliminating the clutter component, a method is known by which a fitting process is performed, by using a polynomial such as a Legendre polynomial, on time-series data of obtained In-phase Quadrature-phase (IQ) signals, so as to identify a component corresponding to one or more lower degrees as a clutter component. However, when this method is used, the level of precision in identifying the clutter component may be insufficient.

DETAILED DESCRIPTION

An ultrasound diagnosis apparatus according to an embodiment includes processing circuitry. The processing circuitry obtains time-series data having complex values based on a reflected wave of an ultrasound wave transmitted by an ultrasound probe and calculates an expansion coefficient in a case in which the obtained time-series data is expressed as a linear sum of a plurality of mathematical functions, the time-series data having, as an argument, a first parameter related to time. The plurality of mathematical functions are mathematical functions that are possible to be generated on a basis of a function family that has, as arguments, the first parameter and a second parameter different from the first parameter.

Exemplary embodiments will be explained below, with reference to the accompanying drawings.

First Embodiment

Figure 1:
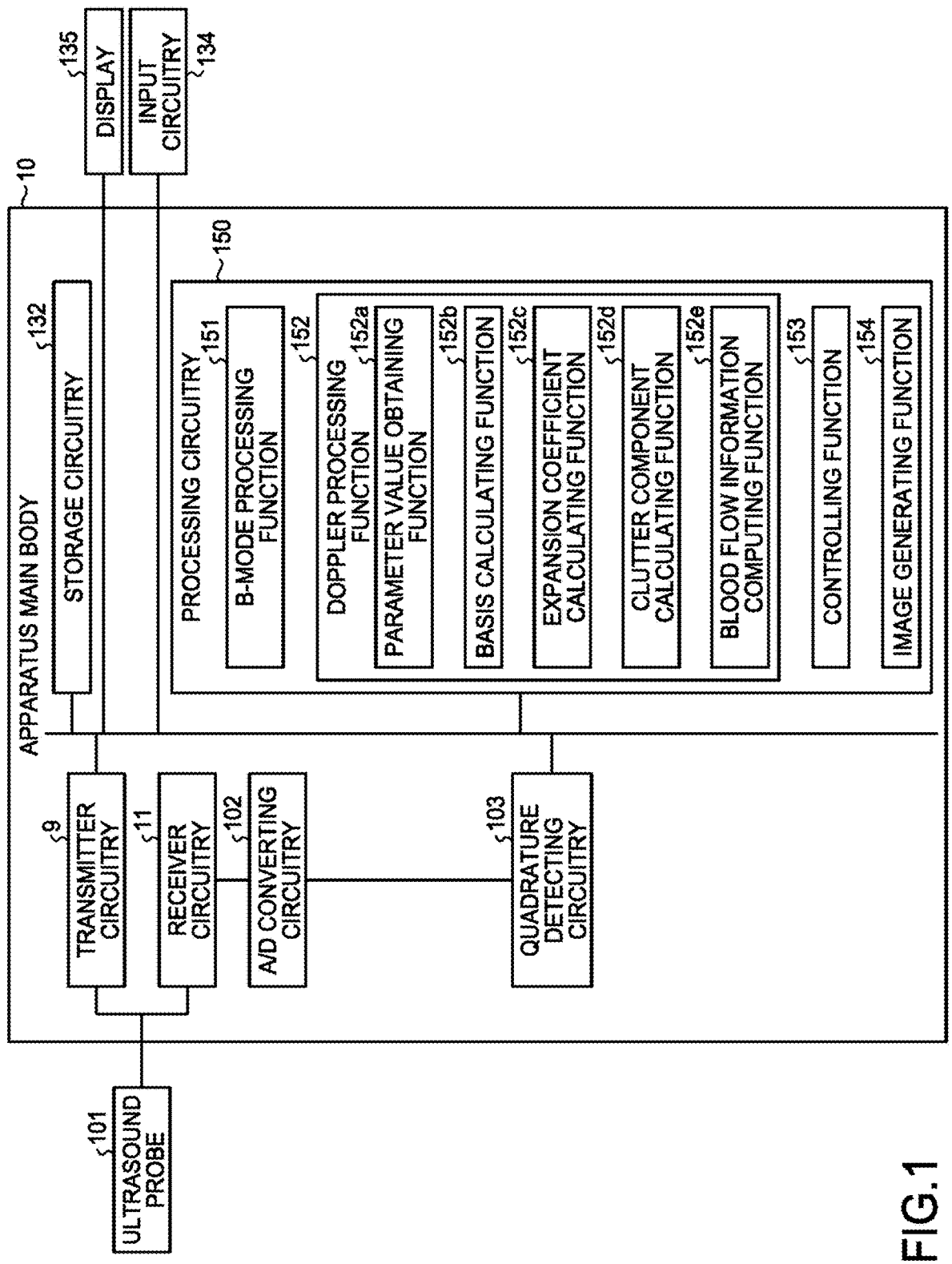
FIG. 1 is a diagram illustrating an ultrasound diagnosis apparatus according to an embodiment.

First, a configuration of an ultrasound diagnosis apparatus according to a first embodiment will be explained. FIG. 1 is a block diagram illustrating an exemplary configuration of the ultrasound diagnosis apparatus according to the first embodiment. As illustrated in FIG. 1, the ultrasound diagnosis apparatus according to the first embodiment includes an ultrasound probe 101, an apparatus main body 10, a display 135, and input circuitry 134.

The ultrasound probe 101 includes a plurality of piezoelectric transducer elements. The plurality of piezoelectric transducer elements are configured to generate an ultrasound wave on the basis of a drive signal supplied thereto from transmitter circuitry 9 (explained later) included in the apparatus main body 10. Further, the plurality of piezoelectric transducer elements included in the ultrasound probe 101 are configured to receive reflected waves from an examined subject (hereinafter, "patient") P and convert the received reflected waves into electrical signals (reflected-wave signals). Further, the ultrasound probe 101 includes matching layers provided for the piezoelectric transducer elements, as well as a backing member or the like that prevents ultrasound waves from propagating rearward from the piezoelectric transducer elements. In this situation, the ultrasound probe 101 is detachably connected to the apparatus main body 10.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected wave by each of the plurality of piezoelectric transducer elements included in the ultrasound probe 101, before being converted into a reflected-wave signal. The amplitude of the reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmitter direction.

The input circuitry 134 includes a mouse, a keyboard, a button, a panel switch, a touch command screen, a foot switch, a trackball, a joystick, and/or the like. The input circuitry 134 is configured to receive various types of setting requests from an operator of the ultrasound diagnosis apparatus and to transfer the received various types of setting requests to the apparatus main body 10.

The display 135 is configured to display a Graphical User Interface (GUI) used by the operator of the ultrasound diagnosis apparatus to input the various types of setting requests through the input circuitry 134 and to display ultrasound image data generated by the apparatus main body 10 or the like.

The apparatus main body 10 is an apparatus configured to generate the ultrasound image data on the basis of the reflected-wave signals received by the ultrasound probe 101. As illustrated in FIG. 1, the apparatus main body 10 includes the transmitter circuitry 9, receiver circuitry 11, Analog/Digital (A/D) converting circuitry 102, quadrature detecting circuitry 103, storage circuitry 132, and processing circuitry 150. The processing circuitry 150 includes a B-mode processing function 151, a Doppler processing function 152, a controlling function 153, and an image generating function 154. More specifically, the Doppler processing function 152 includes a parameter value obtaining function 152a, a basis calculating function 152b, an expansion coefficient calculating function 152c, a clutter component calculating function 152d, and a blood flow information computing function 152e.

The transmitter circuitry 9 includes a rate pulse generator, transmission delay circuitry, and a transmission pulser and is configured to supply the drive signal to the ultrasound probe 101. The rate pulse generator is configured to repeatedly generate a rate pulse used for forming a transmission ultrasound wave, at a predetermined rate frequency. The rate pulses apply a voltage to the transmission pulser, while having mutually-different transmission delay periods as a result of going through the transmission delay circuitry. In other words, the transmission delay circuitry is configured to apply a transmission delay period that is required to converge the ultrasound wave generated by the ultrasound probe 101 into the form of a beam and to determine transmission directionality and that corresponds to each of the piezoelectric transducer elements, to each of the rate pulses generated by the rate pulse generator. The ultrasound wave converged in the form of a beam will be referred to as an "ultrasound beam".

The transmission pulser is configured to apply the drive signal (a drive pulse) to the ultrasound probe 101 with timing based on the rate pulses. The drive pulse travels from the transmission pulser to the piezoelectric transducer elements included in the ultrasound probe 101 via a cable and is subsequently converted from the electric signals into mechanical vibrations in each of the piezoelectric transducer elements. The mechanical vibrations are transmitted as ultrasound waves within the patient's body. In this situation, the ultrasound waves having mutually-different transmission delay periods in correspondence with the piezoelectric transducer elements are converged and are propagated in predetermined directions. In other words, by varying the transmission delay periods applied to the rate pulses, the transmission delay circuitry is able to arbitrarily adjust the transmission directions from the surfaces of the piezoelectric transducer elements.

The transmitter circuitry 9 is configured to apply transmission directionality by controlling a transmission opening (the number and the positions of the piezoelectric transducer elements used when an ultrasound beam is transmitted), by employing the controlling function 153 included in the processing circuitry 150. The transmitter circuitry 9 moves the transmission opening every time ultrasound transmissions corresponding to one scanning line are completed. Further, the transmitter circuitry 9 is configured to converge the ultrasound waves into the form of a beam by controlling the timing with which the piezoelectric transducer elements at the transmission opening are driven, with the use of the transmission delay circuitry.

The transmitter circuitry 9 has a function that is able to instantly change the transmission frequency, the transmission drive voltage, and the like, for the purpose of executing a predetermined scanning sequence on the basis of an instruction from the controlling function 153 (explained later). In particular, the function to change the transmission drive voltage is realized by using a linear-amplifier-type transmitter circuitry of which the value can be instantly switched or by using a mechanism configured to electrically switch between a plurality of power source units.

When the ultrasound diagnosis apparatus is configured with a Doppler mode, the ultrasound diagnosis apparatus is configured, for example, to emit ultrasound pulses onto the patient as many times as K via the ultrasound probe 101 including a plurality of ultrasound piezoelectric elements, where K is an integer expressing the number of times of transmissions corresponding to one packet (a set of data obtained when a plurality of reflected echo signals (the reflected waves) having mutually the same depth are arranged in a time series).

The receiver circuitry 11 is configured to receive the reflected-wave signals from the ultrasound probe 101. For example, in the Doppler mode, the packet including as many reflected echo signals (reflected waves) as K, which are the reflections of the ultrasound beams emitted onto the patient P, is converted into electrical signals by the ultrasound probe 101.

More specifically, after the reflected waves of the ultrasound waves transmitted by the ultrasound probe 101 have reached the piezoelectric transducer elements provided on the inside of the ultrasound probe 101, the reflected waves are converted in the piezoelectric transducer elements from the mechanical vibrations into the electric signals (the reflected-wave signals) and are then input to the receiver circuitry 11. The receiver circuitry 11 includes a pre-amplifier and reception delay adding circuitry and is configured to generate reflected-wave data, which is analog data, by performing various types of processing processes on the reflected-wave signals received by the ultrasound probe 101.

The pre-amplifier is configured to perform a gain adjusting process by amplifying the reflected-wave signal for each of the channels. The reception delay adding circuitry is configured to apply a reception delay period required to determine reception directionality, to the reflected-wave signals. The reception delay adding circuitry generates the reflected-wave data by performing an adding process (a phase matched adding process) on the reflected-wave signals of which the temporal phases are matched by the application of the reception delay periods. As a result of the phase-matched adding process performed by the reception delay adding circuitry, reflected components from the direction corresponding to the reception directionality of the reflected-wave signals are enhanced.

The receiver circuitry 11 is configured to apply the reception directionality by controlling a reception opening (the number and the positions of the piezoelectric transducer elements used when the reflected-wave signals are received) by employing the controlling function 153. The receiver circuitry 11 moves the reception opening every time the transmission opening is moved. The receiver circuitry 11 is configured to generate reflected-wave data corresponding to one scanning line, by performing the phased-matched adding process on the reflected-wave signals received by the piezoelectric transducer elements at each reception opening.

In the manner described above, the transmitter circuitry 9 and the receiver circuitry 11 control the transmission directionality and the reception directionality of the transmissions and the receptions of the ultrasound waves.

The A/D converting circuitry 102 is configured to convert a sequence of acquired signals received by the receiver circuitry 11 into digital signals. Further, the quadrature detecting circuitry 103 is configured to convert the reflected-wave data received by the receiver circuitry 11 into an In-phase signal ("I signal") and a Quadrature-phase signal ("Q signal") in a baseband. For example, the I signal is a signal corresponding to a cosine part (a real part) of a Doppler-shifted wave, whereas the Q signal is a signal corresponding to a sine part (an imaginary part) of the Doppler-shifted wave.

By employing the Doppler processing function 152, the processing circuitry 150 is configured to generate data (Doppler data) obtained by extracting motion information of mobile members (blood flows, tissues, contrast agent echo components, and the like) based on the Doppler effect, by performing a frequency analysis on the reflected-wave data that has been converted into the digital data by the A/D converting circuitry 102 and the quadrature detecting circuitry 103. More specifically, as the motion information of the mobile members, the Doppler processing function 152 generates the Doppler data obtained by extracting an average velocity value, a dispersion value, a power value, and the like from each of multiple points.

While the Doppler mode is selected, a plurality of pieces of reflected-wave data are acquired by transmitting an ultrasound wave multiple times on the same scanning line. Accordingly, in this configuration, the quadrature detecting circuitry 103 generates a plurality of IQ signals on multiple sampling points positioned on mutually the same scanning line.

In the Doppler mode, a sequence of a plurality of IQ signals obtained by arranging, in a time series, the pieces of reflected-wave data from mutually the same depth corresponding to the pieces of data resulting from the emissions performed multiple times in mutually the same direction will be referred to as a "packet". By employing the Doppler processing function 152, the processing circuitry 150 generates the packet on the basis of the reflected-wave data received by the receiver circuitry 11.

More specifically, the Doppler processing function 152 included in the processing circuitry 150 includes the parameter value obtaining function 152a, the basis calculating function 152b, the expansion coefficient calculating function 152c, the clutter component calculating function 152d, and the blood flow information computing function 152e. Details of these functions will be explained later.

The B-mode processing function 151 is configured to generate data (B-mode data) in which signal intensities (amplitude intensities) are expressed by degrees of brightness, by performing a logarithmic amplification, an envelope detection, a logarithmic compression, and/or the like on the reflected-wave data that has been converted into the digital data by the A/D converting circuitry 102 and the quadrature detecting circuitry 103. Further, the B-mode processing function 151 is capable of varying the frequency band to be rendered in images, by varying the detected frequency.

In an embodiment, processing functions performed by the B-mode processing function 151, the Doppler processing function 152, the controlling function 153, and the image generating function 154 are stored in the storage circuitry 132 in the form of computer-executable programs. The processing circuitry 150 is a processor configured to realize the functions corresponding to the programs, by reading and executing the programs from the storage circuitry 132. In other words, the processing circuitry 150 that has read the programs has the functions illustrated within the processing circuitry 150 in FIG. 1. Further, with reference to FIG. 1, the example was explained in which the single processing circuitry (i.e., the processing circuitry 150) realizes the processing functions of the B-mode processing function 151, the Doppler controlling function 152, the controlling function 153, and the image generating function 154; however, it is also acceptable to structure the processing circuitry 150 by combining together a plurality of independent processors, so that the processors realize the functions by executing the programs.

In other words, it is acceptable to structure each of the abovementioned functions as a program so that single processing circuitry executes the programs. Alternatively, it is also acceptable to install one or more specific functions in a dedicated and independent program executing circuitry.

The term "processor" used in the above explanations denotes, for example, a Central Processing Unit (CPU), a Graphical Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor realizes the functions by reading and executing the programs stored in the storage circuitry 132.

Alternatively, it is also acceptable to directly incorporate the programs into the circuitry of the processor, instead of storing the programs in the storage circuitry 132. In that situation, the processor realizes the functions by reading and executing the programs incorporated in the circuitry thereof.

Further, the expansion coefficient calculating function 152c, the clutter component calculating function 152d, the basis calculating function 152b, and the image generating function 154 are examples of a first calculating unit, a second calculating unit, a third calculating unit, and an image generating unit, respectively. The input circuitry 134 is an example of an input unit. Further, the receiver circuitry 11, the A/D converting circuitry 102, and the quadrature detecting circuitry 103 are examples of a generating unit.

By employing the controlling function 153, the processing circuitry 150 is configured to control the overall processing of the ultrasound diagnosis apparatus. More specifically, by employing the controlling function 153, the processing circuitry 150 is configured to control processes performed by the transmitter circuitry 9, the receiver circuitry 11, the B-mode processing function 151, the Doppler processing function 152, and the image generating function 154, on the basis of the various types of setting requests input by the operator via the input circuitry 134 and various types of control programs and various types of data read from the storage circuitry 132.

Further, by employing the controlling function 153, the processing circuitry 150 is configured to exercise control so that display-purpose ultrasound image data stored in the storage circuitry 132 is displayed on the display 135. For example, the storage circuitry 132 may be a semiconductor memory element such as a Random Access Memory or may be a storage device such as a hard disk, an optical disk, or the like. The B-mode processing function 151, the quadrature detecting circuitry 103, and the processing circuitry 150 may each be, for example, an electronic circuit such as a Central Processing Unit (CPU) or a Micro Processing Unit (MPU) or an integrated circuit such as an Application Specific Integrated Circuit (ASIC) or a Field Programmable Gate Array [FPGA].

By employing the image generating function 154, the processing circuitry 150 is configured to generate ultrasound image data from the data generated by the B-mode processing function 151 and the Doppler processing function 152. In other words, the processing circuitry 150 including the image generating function 154 generates B-mode image data in which intensities of the reflected waves are expressed by degrees of brightness, from the B-mode data generated by the processing circuitry 150 while employing the B-mode processing function 151. Further, the image generating function 154 generates an average velocity image, a dispersion image, and a power image each expressing mobile member information or color Doppler image data representing an image combining any of these images, from the Doppler data generated by the processing circuitry 150 while employing the Doppler processing function 152.

In this situation, generally speaking, by employing the image generating function 154, the processing circuitry 150 converts (by performing a scan convert process) a scanning line signal sequence from an ultrasound scan into a scanning line signal sequence in a video format used by, for example, television and generates the display-purpose ultrasound image data. More specifically, by employing the image generating function 154, the processing circuitry 150 generates the display-purpose ultrasound image data by performing a coordinate transformation process compliant with the ultrasound scanning mode used by the ultrasound probe 101. Further, by employing the image generating function 154, the processing circuitry 150 combines text information of various parameters, scale graduations, body marks, and the like with the ultrasound image data. By employing the image generating function 154, the processing circuitry 150 is capable of generating a three-dimensional B-mode image by performing a coordinate transformation process on three-dimensional B-mode data generated by the B-mode processing function 151. Further, by employing the image generating function 154, the processing circuitry 150 is capable of generating a three-dimensional color Doppler image by performing a coordinate transformation process on three-dimensional Doppler data generated by the Doppler processing function 152. Furthermore, by employing the image generating function 154, the processing circuitry 150 is also capable of generating display-purpose two-dimensional ultrasound image data, by performing any of various types of rendering processes on three-dimensional image data.

The storage circuitry 132 is a memory configured to store therein the image data generated by the processing circuitry 150 while employing the image generating function 154. Further, the storage circuitry 132 is capable of storing therein the data generated by the processing circuitry 150 while employing the B-mode processing function 151 or the Doppler processing function 152.

Next, a background of the first embodiment will briefly be explained.

Examples of modes used in ultrasound diagnosis processes performed by ultrasound diagnosis apparatuses include the Doppler mode. In the Doppler mode, an ultrasound probe emits an ultrasound wave multiple times in mutually the same direction toward a site serving as an observation target that is moving at predetermined velocity, so that the velocity of a blood flow component, for example, is calculated by detecting a frequency shift (a Doppler change) caused by the Doppler effect.

Mixed with a signal of the blood flow component serving as the observation target, reception signals in the Doppler mode include a signal called a clutter component, which originates from tissues that are either stationary or moving at low velocity. Usually, the signal intensity of a clutter component is higher than the signal intensity of the blood flow component, by tens to hundreds of decibels (dB). For this reason, in order to extract the signal of the blood flow component, the clutter component is eliminated.

Figure 2:
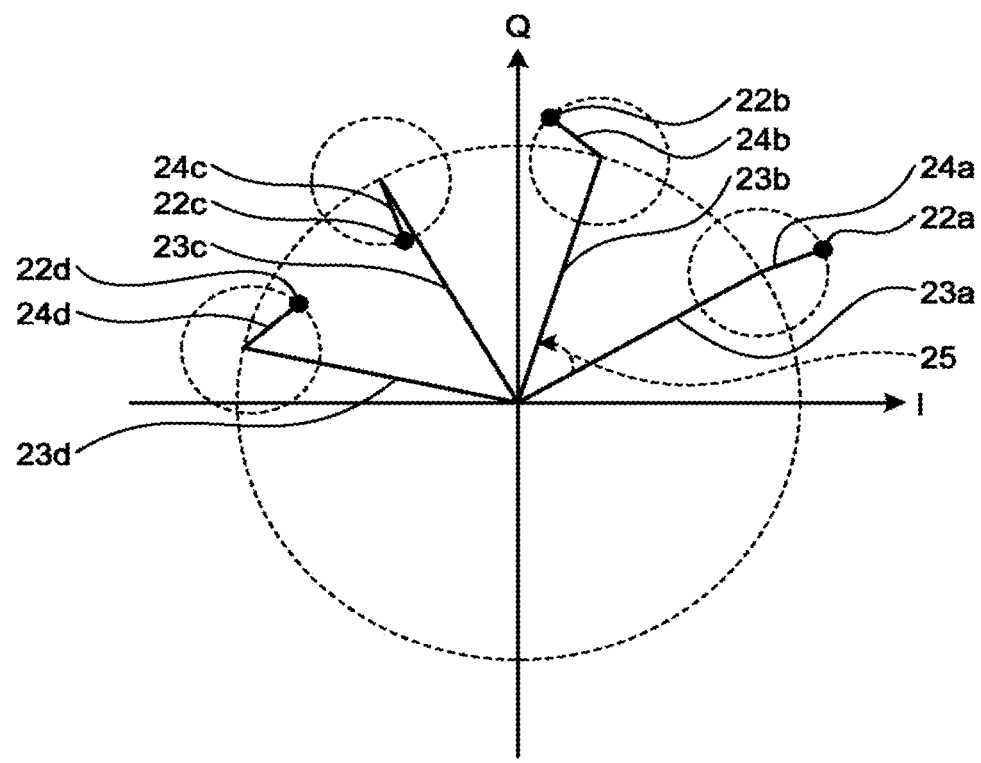
FIG. 2 is a drawing for explaining a background of the embodiment.

FIG. 2 illustrates the situation described above. FIG. 2 is a drawing for explaining the background of the embodiment. In FIG. 2, the point 22a expresses IQ signals at a time t=0. The value of the real part and the value of the imaginary part of the point 22a on a complex number plane correspond to the magnitude of the I signal and the magnitude of the Q signal, respectively. Further, the point 22b expresses IQ signals at a time t=1. Each of the points 22c and 22d expresses IQ signals at a corresponding one of the times t=2 and t=3.

The vector 23a is a vector expressing a clutter component in the IQ signals at the time t=0. The vector 23b is a vector expressing a clutter component in the IQ signals at the time t=1. Each of the vectors 23c and 23d is a vector expressing a clutter component in the IQ signals at a corresponding one of the times t=2 and t=3.

The vector 24a is a vector expressing a blood flow signal in the IQ signals at the time t=0. The vector 24b is a vector expressing a blood flow signal in the IQ signals at the time t=1. Further, each of the vectors 24c and 24d is a vector expressing a blood flow signal in the IQ signals at a corresponding one of the times t=2 and t=3.

For example, at the time t=0, it is possible to calculate the vector 24a expressing the blood flow signal, by subtracting the vector 23a expressing the clutter component from a position vector of the point 22a expressing the magnitude of the IQ signals. Similarly, at the times t=1, 2, and 3, it is possible to calculate each of the vectors 24b, 24c, and 24d expressing the blood flow signals, by subtracting a corresponding one of the vectors 23b, 23c, and 23d expressing the clutter components, from the position vector of a corresponding one of the points 22b, 22c, and 22d expressing the magnitudes of the IQ signals.

In this situation, because the magnitudes of the vectors 24a to 24d expressing the targeted blood flow signals are smaller than the magnitudes of the vectors 23a to 23d expressing the clutter components, the contributions of the targeted blood flow signals to the IQ signals are small. Accordingly, how properly the clutter component can be eliminated has an impact on the quality of the image rendering the blood flow signals.

As a method for eliminating the clutter component, a method called a polynomial fitting method is known by which a fitting process is performed by using a predetermined polynomial on time-series data of obtained IQ signals so as to identify components of small degrees as a clutter component. As another example, a method called complex Legendre method is also known. However, when these methods are used, the level of precision in the extraction of the clutter component may be insufficient.

For example, when the polynomial fitting method is used, estimation of a clutter and estimation of suppression of a clutter that are realized by performing a least-squares fitting process may be insufficient. Further, in the estimation and the suppression of the clutter component according to the polynomial fitting method, it is not possible to distinguish between positive velocity values and negative velocity values. More specifically, the phases of the IQ signals observed in the Doppler mode fluctuate with positive/negative signs corresponding to the positive/negative values of the velocity of the measurement target object. In other words, a signal approaching the probe exhibits a positive phase change, whereas a signal moving away from the probe exhibits a negative phase change. However, the mathematical function system used in the polynomial fitting method is a real-number polynomial function system. When the IQ signals, which are complex signals, are expressed by using a real-number function system, it means that it is not possible to distinguish between a positive phase and a negative phase. For this reason, the real-number polynomial function system is not able to distinguish between two measurement target objects of which the signals have an equal absolute value (i.e., equal amplitude) but have velocity values with mutually-different signs. As a result, it is more difficult to distinguish between a clutter component and a blood flow signal of which the intensities are significantly different.

Further, complex Legendre method has an advantage over the polynomial fitting method because it is possible to better estimate velocity values with signs. However, because the capability of expressing clutters are not different from that of the polynomial fitting method, the level of precision for the estimation and the suppression of the clutters may not be improved so much in some situations.

In view of the background described above, an ultrasound diagnosis apparatus according to an embodiment is configured to eliminate (suppress) the clutter component, by calculating an expansion coefficient in a case in which IQ signals arranged in a time series (the signals in one packet) are expressed as a linear sum of a plurality of predetermined mathematical functions. In this situation, the plurality of predetermined mathematical functions are mathematical functions that are possible to be generated on the basis of a function family that has a first parameter t related to time and a second parameter $\phi$ different from the first parameter t as arguments.

Figure 3:
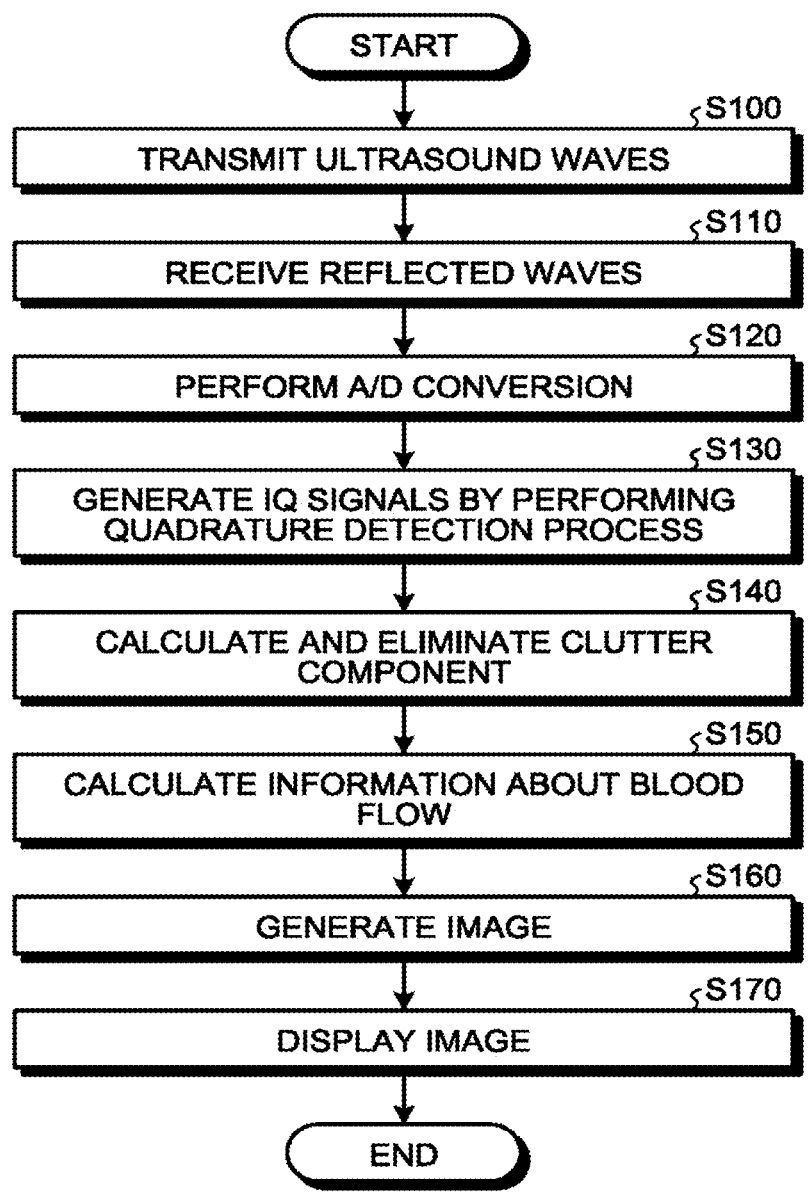
FIGS. 3 and 4 are drawings for explaining a flow in a process performed by an ultrasound diagnosis apparatus according to a first embodiment.
Figure 4:
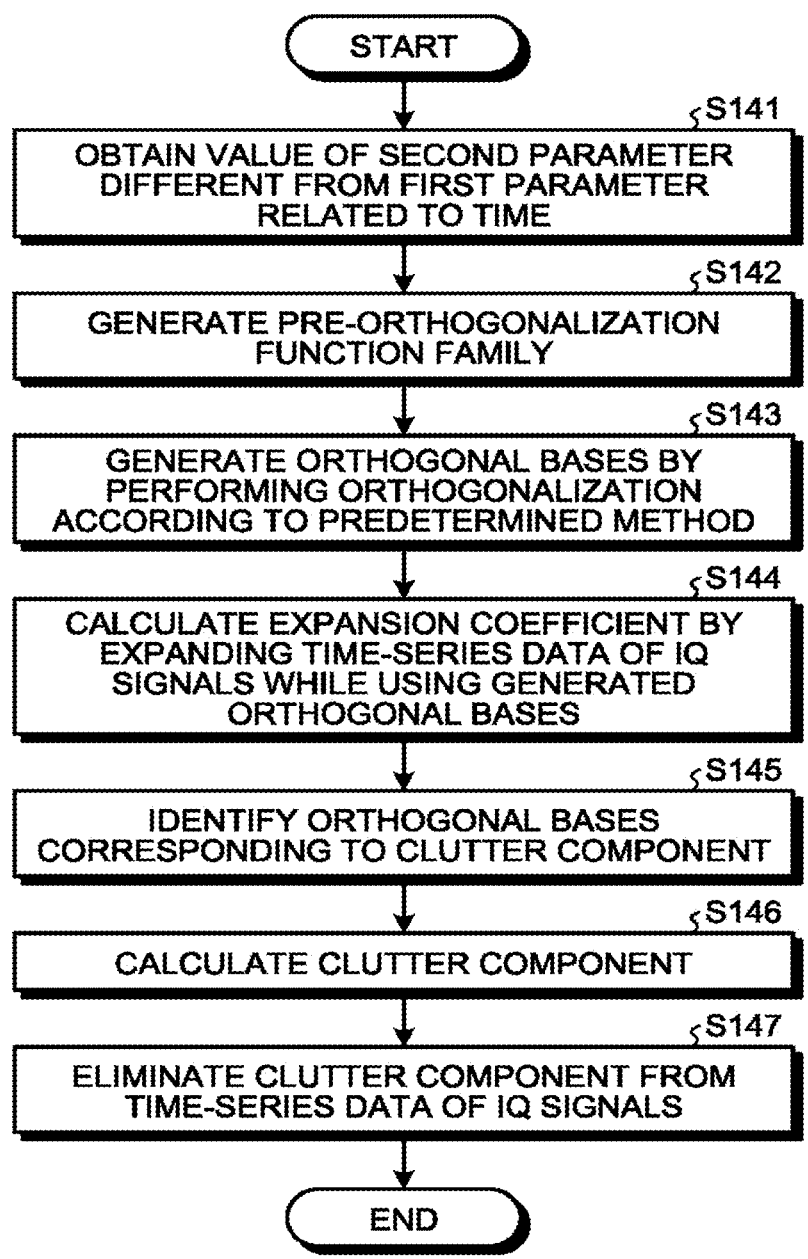

A procedure in a process performed by the ultrasound diagnosis apparatus according to the first embodiment will be explained, with reference to FIGS. 3 and 4. FIGS. 3 and 4 are drawings for explaining a flow in the process performed by the ultrasound diagnosis apparatus according to the first embodiment.

First, the transmitter circuitry 9 causes the ultrasound probe 101 to transmit a plurality of ultrasound waves corresponding to one packet toward the patient P (step S100). The receiver circuitry 11 receives, via the ultrasound probe 101, reflected waves each corresponding to a different one of the plurality of ultrasound waves transmitted toward the patient at step S100 (step S110). The A/D converting circuitry 102 performs an A/D conversion on the reflected waves received by the receiver circuitry 11 at step S110 (step S120). The quadrature detecting circuitry 103 generates IQ signals by performing a quadrature detection process on the data resulting from the A/D conversion performed at step S120 (step S130). In other words, the A/D converting circuitry 102 and the quadrature detecting circuitry 103 structuring the generating unit generate time-series data having complex values that has the first parameter related to time as an argument, on the basis of the reflected waves of the ultrasound waves transmitted by the ultrasound probe 101. The processing circuitry 150 obtains the time-series data having the complex values generated in this manner. Subsequently, the processing circuitry 150 calculates and eliminates a clutter component by employing the parameter value obtaining function 152a, the basis calculating function 152b, the expansion coefficient calculating function 152c, and the clutter component calculating function 152d (step S140). The process at this step will be explained in detail, with reference to FIG. 4. Further, by employing the blood flow information computing function 152e, the processing circuitry 150 calculates information about the blood flow by subtracting the clutter component calculated at step S140 from the time-series data of the IQ signals generated at step S130 (step S150). After that, by employing the image generating function 154, the processing circuitry 150 generates an image from the information about the blood flow calculated at step S150, i.e., a signal component obtained by subtracting the clutter component calculated at step S140 from the time-series data of the IQ signals generated at step S130 (step S160). The display 135 receives data of the image generated at step S160 from the processing circuitry 150 and displays the image (step S170).

Next, the operation at step S140 will be explained in detail, with reference to FIG. 4. FIG. 4 is a drawing for explaining in details the process at step S140 in FIG. 3.

First, by employing the parameter value obtaining function 152a, the processing circuitry 150 obtains the value of the second parameter $\phi$ that is different from the first parameter t related to time (step S141). In an example, the second parameter $\phi$ may be a parameter calculated on the basis of a phase change in the clutter. For example, the second parameter $\phi$ is an estimated value of a phase change in the clutter per unit time period. For example, the second parameter $\phi$ is a value set in the range of $-\pi<\phi<+\pi$, as a value indicating at what velocity the clutter is measured, when the range of the estimated velocity of the clutter (the velocity of the measurement target object detectable in the Doppler mode), i.e., the amount of change in the phase among the IQ signals in the measured packet, is expressed as $-\pi$ to $+\pi$.

Further, the input circuitry 134 may receive an input of the value of the second parameter $\phi$ from the user. Alternatively, the processing circuitry 150 may obtain the value of the second parameter $\phi$ from the storage circuitry 132. In that situation, the value of the second parameter $\phi$ may be, for example, stored in the storage circuitry 132 in advance for each of the body sites that are imaged, as an empirical value that is known in advance for each of the body sites that are imaged.

Further, the input circuitry 134 may calculate the value of the second parameter $\phi$, on the basis of a set value for a flow rate range (the highest velocity in the positive direction and the highest velocity in the negative direction with respect to the velocity of the object of interest, such as a blood flow, observed in a region of interest) of the ultrasound diagnosis apparatus. Alternatively, the input circuitry 134 may calculate the value of the second parameter φ, on the basis of both the body site to be imaged and the set value for the flow rate range.

Subsequently, the processing circuitry 150 generates a function family A prior to an orthogonalization process (hereinafter, "pre-orthogonalization function family A"), on the basis of the values of the first parameter t related to time and the second parameter φ (step S142). The pre-orthogonalization function family A can be expressed as indicated in Expression (1) below, for example:

$$A=[C_0, C_1, C_2, C_3 \ldots, C_m, \ldots] \quad (1)$$

In Expression (1), $C_m(t)$ denotes an m-th function among the mathematical functions (hereinafter, "functions", as appropriate) belonging to the function family A, where m is an integer of 0 or larger. $C_m(t)$ is a function of the first parameter t related to time. $C_m(t)$ is a function that exhibits complex values, for example.

For instance, a specific example of the function system of $C_m(t)$ can be expressed as indicated in Expression (2) below:

$$C_m(t)=f(t)^m \quad (2)$$

In Expression (2), f(t) is a predetermined function related to the first parameter t. In this situation, an indicator of the pre-orthogonalization function family A can be expressed as indicated in Expression (3) below:

$$A=[1, f(t), f(t)^2, f(t)^3, \ldots, f(t)^m, \ldots] \quad (3)$$

In this situation, a specific example of f(t) can be expressed as indicated in Expression (4) below, for example:

$$f(t)=te^{j\phi t} \quad (4)$$

In Expression (4), the letter "e" denotes the natural logarithm, whereas the letter "j" denotes the imaginary unit, and the letter "φ" denotes the second parameter φ explained above. When the expression is at the limit on the assumption that φ is not present (i.e., φ=0), f(t)=t is satisfied. In other words, while using the situation f(t)=t as the reference, Expression (4) corrects the function system of f(t) by using the second parameter φ according to a predetermined method. In this situation, a specific expression of the pre-orthogonalization function family A can be written as indicated in Expression (5) below, for example:

$$A=[1, te^{j\phi t}, t^2 e^{j(2\phi t)}, t^3 e^{j(3\phi t)}, \ldots, t^m e^{j(m\phi t)}, \ldots] \quad (5)$$

When f(t) is not a constant, the elements $C_m(t)$ of the pre-orthogonalization function family A are linearly independent. When the elements $C_m(t)$ of the pre-orthogonalization function family A are defined in a predetermined region, it is possible to define a predetermined inner product with respect to the function. For example, when $C_m(t)$ exhibits complex values, it is possible to define a Hermitian inner product with respect to the function. In this situation, by applying a process known as a Schmidt orthogonalization process to each of the elements of the pre-orthogonalization function family A under the defined inner product, it is possible to generate orthonormal bases.

In other words, by employing the basis calculating function 152b, the processing circuitry 150 generates a set B of orthogonal bases, by performing the orthogonalization process on the pre-orthogonalization function family A according to the predetermined method under the predetermined inner product (step S143). More explicitly, the set B of orthogonal bases can be expressed as indicated in Expression (6) below, for example:

$$B=[e_0(t), e_1(t), e_2(t), \ldots, e_n(t), \ldots] \quad (6)$$

In Expression (6), the letter "e" denotes being an orthonormal basis. In other words, $e_n(t)$ is an n-th orthonormal function, which is a function of the first parameter t, where n is a natural number. The orthonormal basis $e_n(t)$ may be, for example, a function that exhibits complex values. In this situation, in an example, the orthonormality can be expressed as indicated in Expression (7) below, for example.

$$\int_{-1}^{1} dt\, e^*_i(t) e_j(t) = \delta_{ij} \quad (7)$$

In Expression (7), i and j are each a predetermined natural number. The symbol "*" expresses a complex conjugate. The letter "δ" denotes a Kronecker delta. In other words, when i=j is satisfied, the integration on the left-hand side of Expression (7) is equal to 1. On the contrary, when i≠j is satisfied, the integration on the left-hand side of Expression (7) is equal to 0. Accordingly, it is considered that Expression (7) is an expression in which the concept of the Hermitian inner product regarding points is naturally generalized with respect to the function.

To explain the meaning of Expression (4), let us discuss at first the situation based on the assumption that the second parameter φ is not present (i.e., φ=0). In that situation, it is possible to simplify Expression (4) as indicated in Expression (8) below:

$$f(t)=t \quad (8)$$

In this situation, a specific expression of the pre-orthogonalization function family A can be written as indicated in Expression (9) below:

$$A=[1, t, t^2, t^3, \ldots, t^m] \quad (9)$$

In this situation, with respect to a closed interval [−1 to 1], when an inner product is naturally introduced to among the functions by using an $L_2$ norm so as to perform an Schmidt orthogonalization on the introduce inner product, it is possible to express the elements of the set B of orthonormal bases with a function $P_n(t)$ in which a Legendre polynomial is multiplied by a predetermined normalization constant, as indicated in Expression (10) below:

$$B=[P_0(t), P_1(t), P_2(t), \ldots, P_n(t), \ldots] \quad (10)$$

In other words, in Expression (4), the letter "t" on the right-hand side is a term for generating the Legendre polynomial after the Schmidt orthogonalization is performed. In this situation, "exp(jφt)" on the right-hand side of Expression (4) is a term for correcting the clutter component. In other words, when the second parameter φ expresses the phase change in the clutter per a unit time period, exp(jφt) serves as a term expressing the effect of incorporating, in the pre-Schmidt-orthogonalization function family, an effect where the phase of the time-series data of the IQ signals changes in the course of time, due to the fact that the phase change φ in the clutter per unit time period is finite. As a result, because the Schmidt orthogonalization is performed while the term exp(jφt) is included, the generated orthonormal basis expressed as $e_i(t)$ is an orthonormal basis incorporating the phase change φ in the clutter per unit time period. Accordingly, by expanding the time-series data of the IQ signals while using these bases, it is possible to improve the level of precision in the estimation of the clutter component.

After that, by employing the expansion coefficient calculating function 152c, the processing circuitry 150 calculates an expansion coefficient $\omega_i$ by expanding the time-series data I(t)+jQ(t) of the IQ signals by using the generated orthogonal bases $e_i(t)$ (step S144). This situation can be expressed as indicated in Expression (11) below, for example:

$$I(t) + jQ(t) = \sum_i \omega_i e_i(t) \quad (11)$$

In Expression (11), I(t) denotes a signal in the real-number part within the time-series data of the IQ signals. Q(t) denotes a signal of the imaginary-part within the time-series data of the IQ signals. The letter "j" denotes the imaginary unit. The orthonormal basis $e_i(t)$ denotes an i-th orthonormal basis. The expansion coefficient $\omega_i$ is an expansion coefficient for the i-th orthonormal basis $e_i(t)$. The orthonormal basis $e_i(t)$ may be a complex number, for example. The expansion coefficient $\omega_i$ may be either a real number or a complex number, for example.

To summarize, by employing the expansion coefficient calculating function 152c, the processing circuitry 150 calculates the expansion coefficient $\omega_i$ in a case in which the time-series data $I(t)+jQ(t)$ of the IQ signals is expressed as a linear sum of the plurality of mathematical functions $e_i(t)$. In this situation, the plurality of mathematical functions $e_i(t)$ are mathematical functions that are possible to be generated on the basis of the function family A that has the first parameter t related to time and the second parameter $\phi$ different from the first parameter t as the arguments. In this situation, the plurality of mathematical functions $e_i(t)$ are mathematical functions that are possible to be generated by implementing a predetermined orthogonalization method such as the Schmidt orthogonalization on the function family A. Further, typically, the plurality of mathematical functions $e_i(t)$ are mathematical functions having values in complex numbers.

A specific expression of the expansion coefficient $\omega_i$ can be written as indicated in Expression (12) below, for example, by using a standard method:

$$\omega_i = \int_{-1}^{1} e^*_i(t)I(t)dt + j\int_{-1}^{1} e^*_i(t)Q(t)dt \quad (12)$$

It is possible to easily confirm the derivation of Expression (12), by using Expression (13) below, for example. Expression (13) uses Expression (7), which is a relation expression for the orthonormal bases.

$$\int_{-1}^{1} e^*_j(t)\{I(t) + jQ(t)\}dt = \int_{-1}^{1} e^*_j(t)\left\{\sum_i \omega_i e_i(t)\right\}dt \quad (13)$$

$$= \sum_i \int_{-1}^{1} e^*_j(t)\omega_i e_i(t)dt$$

$$= \sum_i \omega_i \int_{-1}^{1} e^*_j(t)e_i(t)dt$$

$$= \sum_i \omega_i \delta_{ij}$$

$$= \omega_j$$

Further, as a method for calculating the expansion coefficient $\omega_i$, the processing circuitry 150 may, by employing the expansion coefficient calculating function 152c, numerically project the observation packet (the time-series data $I(t)+jQ(t)$ of as many IQ signals as K) resulting from the quadrature detection process, onto a space defined by the orthonormal bases $e_i(t)$ (where $1 \leq i \leq M$), while M is a pre-determined natural number equal to or smaller than K (which means that M may be equal to K or may be a natural number smaller than K). In that situation, the processing circuitry 150 calculates the expansion coefficient $\omega_i$ by performing a least-squares fitting process, for example, while employing the expansion coefficient calculating function 152c.

Subsequently, by employing the clutter component calculating function 152d, the processing circuitry 150 identifies orthogonal bases corresponding to the clutter component (step S145). In other words, by employing the clutter component calculating function 152d, the processing circuitry 150 identifies the clutter component included in the time-series data $I(t)+jQ(t)$, on the basis of the expansion coefficient $\omega_i$ calculated at step S144.

According to an example of a method for identifying the clutter component, while employing the clutter component calculating function 152d, the processing circuitry 150 identifies a degree $i_{th}$ at which the expansion coefficient $\omega_i$ calculated at step S144 switches from decreasing to increasing as the degree of expansion "i" increases and further identifies the clutter component on the basis of the identified degree $i_{th}$. More specifically, the processing circuitry 150 identifies a component related to the orthonormal bases corresponding to degrees equal to or lower than the identified degree as the clutter component and identifies a component corresponding to degrees higher than the identified degree as the signal component of blood or the like. In other words, on the basis of the notion that the clutter component is expressed in the lower-degree component, whereas the signal component of the blood or the like is expressed in the higher-degree component, the processing circuitry 150 identifies, as the clutter component, the component corresponding to one or more degrees equal to or lower than the degree at which it is possible to separate the lower-degree component and the higher-degree component from each other when the fitting process is performed on the time-series data by using a linear sum of the two components.

According to another example of a method for identifying the clutter component, by employing the clutter component calculating function 152d, the processing circuitry 150 may identify a component corresponding to one or more degrees of expansion equal to or lower than a predetermine degree, as a clutter component. For example, by employing the clutter component calculating function 152d, the processing circuitry 150 may identify the component corresponding to the zeroth and the first degrees of expansion (i.e., the component corresponding to $e_0(t)$ and $e_1(t)$) as the clutter component.

Subsequently, when the degree of the clutter component has been identified at step S145 by employing the clutter component calculating function 152d, the processing circuitry 150 calculates the clutter component on the basis of the identified degree (step S146). After that, the processing circuitry 150 eliminates (subtracts) the clutter component calculated at step S146 from the time-series data of the IQ signals (step S147) so as to extract the data corresponding to the blood flow signal or the like. The extracted data is used for generating the image at step S160 illustrated in FIG. 3. In other words, by employing the image generating function 154, the processing circuitry 150 generates the image (the Doppler image) from the signal component obtained by subtracting the clutter component calculated at step S146 from the time-series data.

Further, by employing the blood flow information computing function 152e, the processing circuitry 150 calculates blood flow information such as the flow rate, the flow volume, the dispersion or the like of the blood flow, by using the signal obtained by extracting the Doppler-shifted blood flow component as a result of eliminating (suppressing) the clutter component. The calculated blood flow information is displayed at step S170 on the subsequent stage, while being superimposed on a B-mode (brightness) image taken at a different time, for example.

Figure 5:
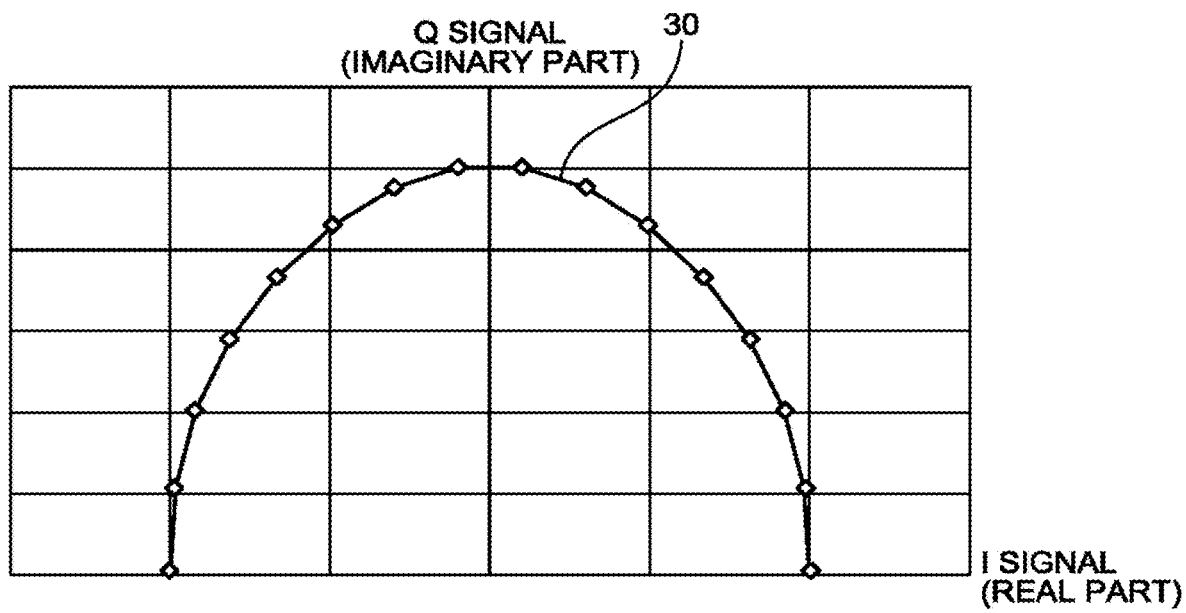
FIG. 5 illustrates an example of data generated for comparing processes performed by ultrasound diagnosis apparatuses according to a conventional technique and the first embodiment.
Figure 6:
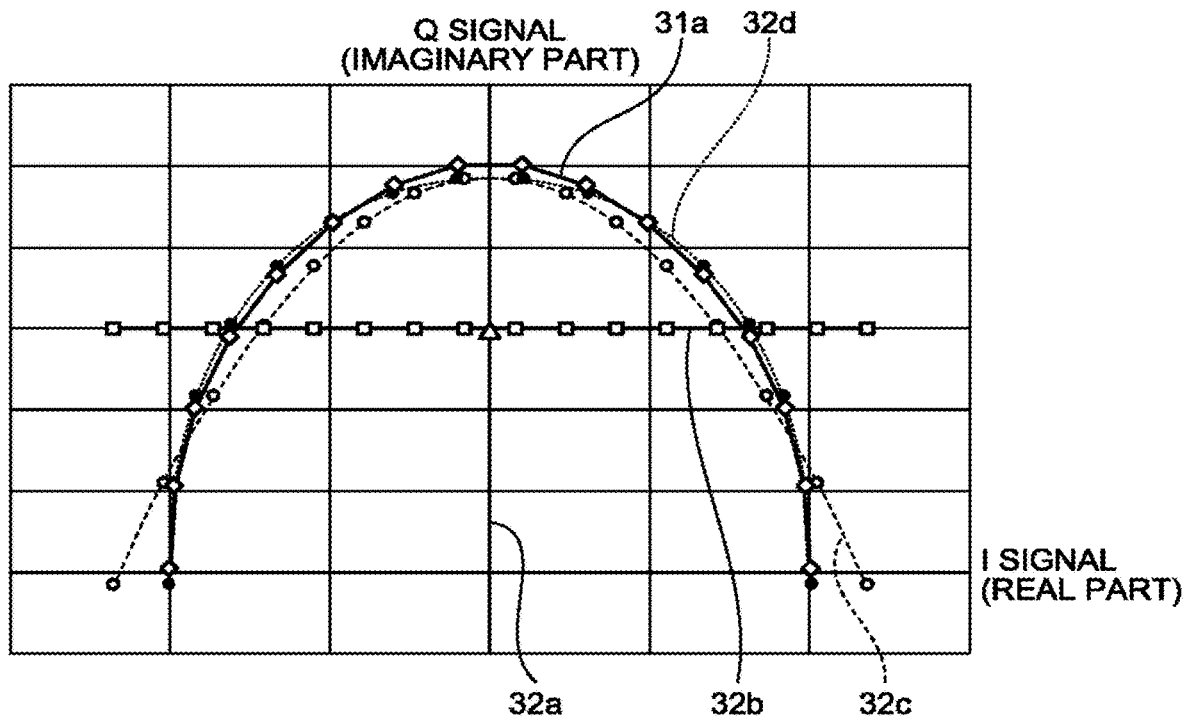
FIG. 6 is a chart for explaining an example of the process performed by the ultrasound diagnosis apparatus according to the conventional technique.
Figure 7:
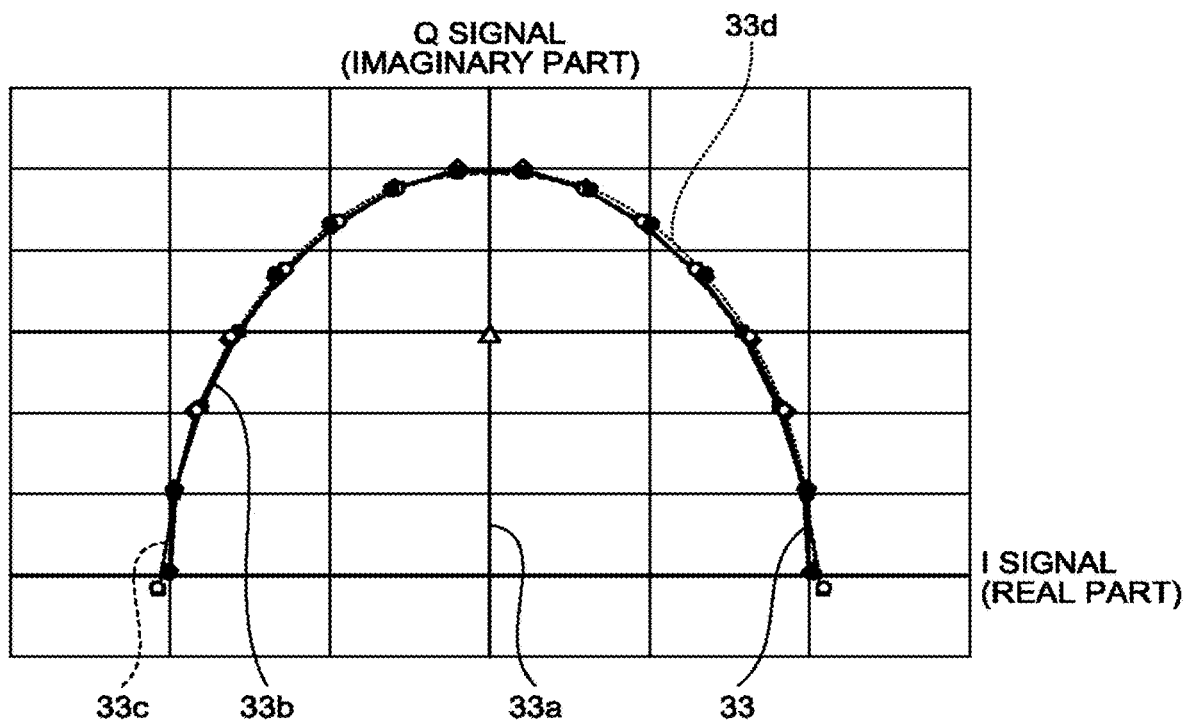
FIG. 7 is a chart for explaining an example of the process performed by the ultrasound diagnosis apparatus according to the first embodiment.
Figure 8:
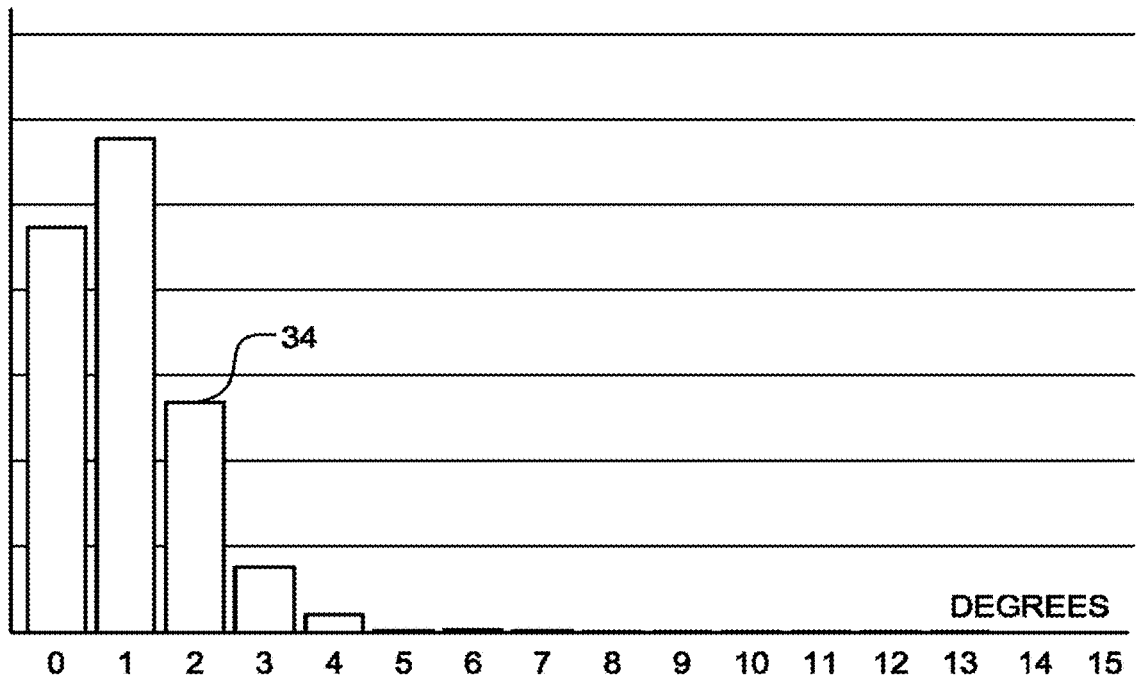
FIG. 8 is another chart for explaining the example of the process performed by the ultrasound diagnosis apparatus according to the conventional technique.
Figure 9:
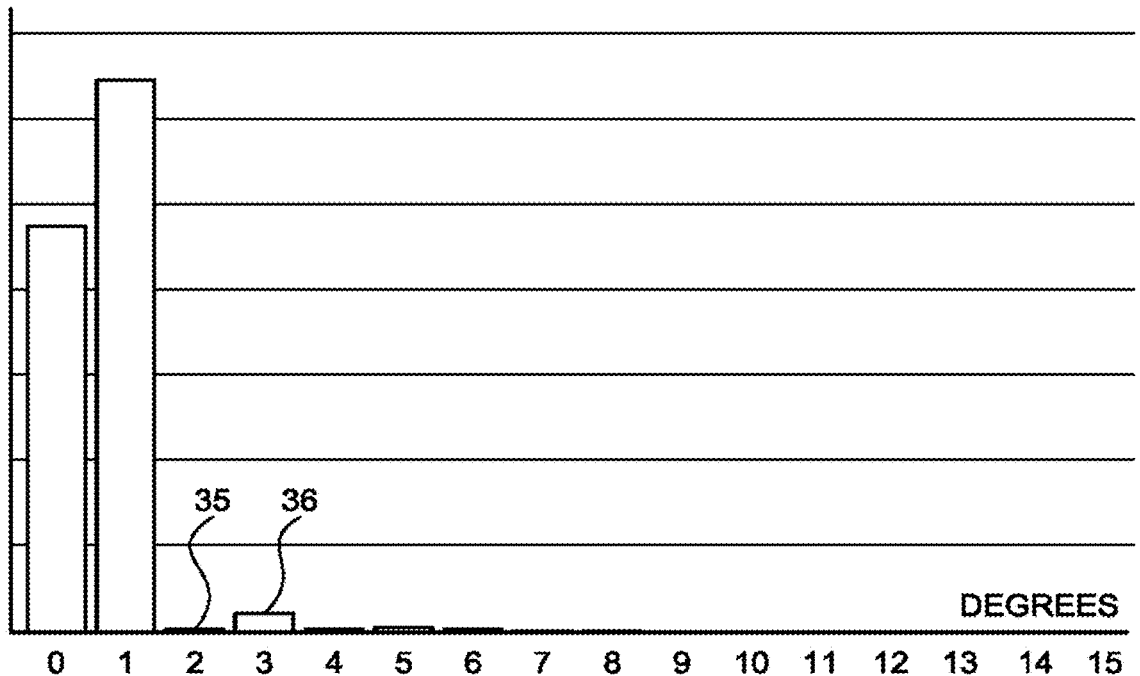
FIG. 9 is another chart for explaining the example of the process performed by the ultrasound diagnosis apparatus according to the first embodiment.
Figure 10:
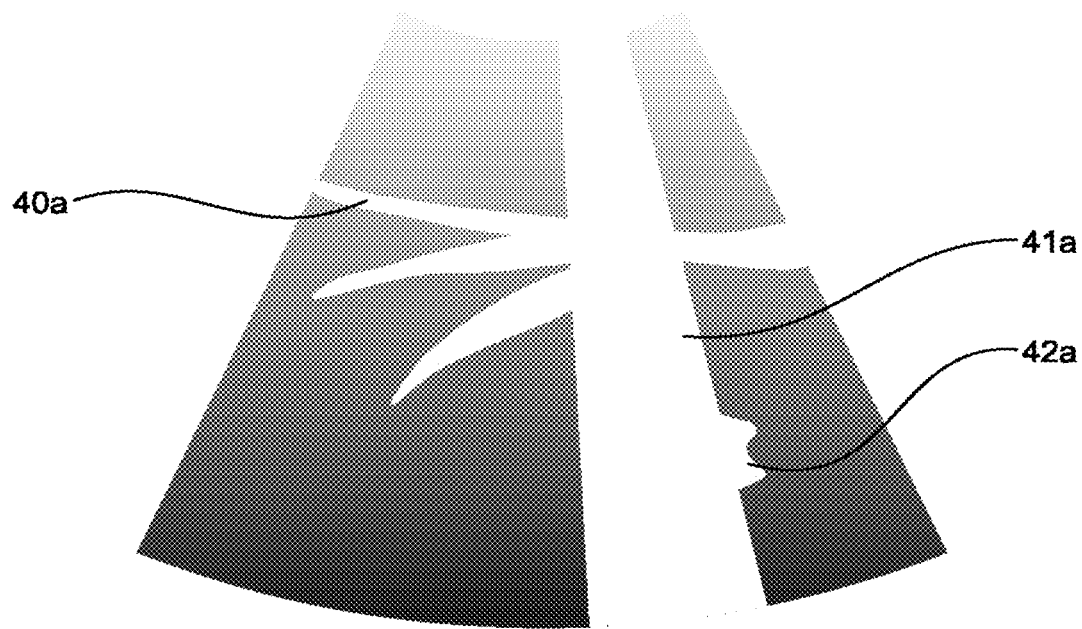
FIG. 10 is a drawing for explaining an example of an image generated by the ultrasound diagnosis apparatus according to the conventional technique.
Figure 11:
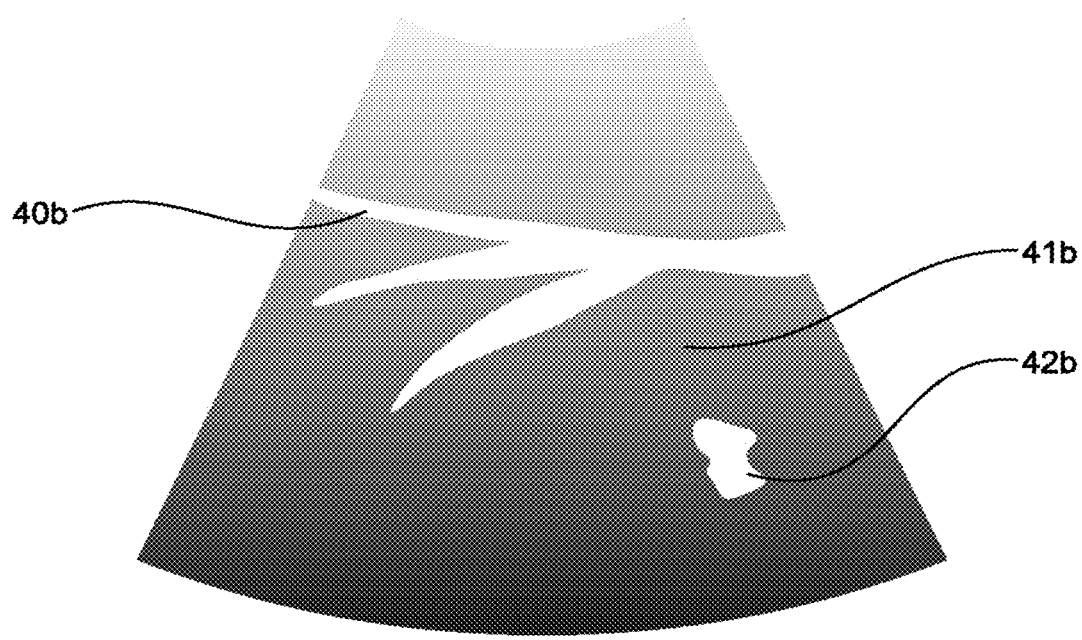
FIG. 11 is a drawing for explaining an example of an image generated by the ultrasound diagnosis apparatus according to the first embodiment.

Next, a specific example of the clutter eliminating (suppressing) process performed by the ultrasound diagnosis apparatus according to the first embodiment will be explained, with reference to FIGS. 5 to 11. FIG. 5 illustrates an example of data generated for comparing processes performed by ultrasound diagnosis apparatuses according to a conventional technique and the first embodiment. FIGS. 6, 8, and 10 are drawings for explaining examples of the process performed by the ultrasound diagnosis apparatus according to the conventional technique. FIGS. 7, 9, and 11 are drawings for explaining examples of the process performed by the ultrasound diagnosis apparatus according to the first embodiment.

FIG. 5 illustrates IQ signals having a packet size of 16 that were generated in a simulation. In other words, FIG. 5 illustrates the IQ signals in the situation where an ultrasound wave is transmitted 16 times (K=16) per packet. The horizontal axis in FIG. 5 expresses the I signal (i.e., the real part of the signal), whereas the vertical axis in FIG. 5 expresses the Q signal (i.e., the imaginary part of the signal). The sixteen diamond-shaped markers in FIG. 5 indicate the sixteen IQ signals in a time-series. The graph 30 is a graph expressing the IQ signals in the time-series. The IQ signals were generated by adding together a clutter of which the amplitude was 1 and the velocity was $\pi/15$ and a blood flow signal of which the amplitude was 0.01 and the velocity was $\pi/4$. FIG. 6 illustrates a result obtained by sequentially performing a fitting process that uses the function according the conventional technique on the IQ signals, starting with the lowest degree. FIG. 7 illustrates a result obtained by sequentially performing a fitting process that uses the orthonormal bases $e_i(t)$ according to the first embodiment on the IQ signals, starting with the lowest degree. As information (phase information) of the second parameter $\phi$ used for designing the pre-orthogonalization function $C_m(t)$, $\pi/15$, which is the velocity of the clutter, was given.

In FIG. 6, the graph 31a is a graph of the signals on which the fitting process is performed. FIG. 6 illustrates results of the fitting process performed on these graphs by using the function according the conventional technique. In the present example, the function according to the conventional technique is a real-number polynomial function expressed as $R_m(t)=t^m$. The graphs 32a, 32b, 32c, and 32d indicate a zeroth-degree component, a first-degree component, a second-degree component, and a third-degree component obtained by using the function according to the conventional technique, respectively.

FIG. 7 illustrates a result obtained by performing the fitting process by using the function according to the first embodiment. In the present example, the function according to the first embodiment is the complex orthonormal basis $e_m(t)$ derived from the complex function $C_m(t)$ by performing the Schmidt orthogonalization. The graphs 33a, 33b, 33c, and 33d indicate a zeroth-degree component, a first-degree component, a second-degree component, and a third-degree component obtained by using the function according to the first embodiment, respectively.

FIG. 8 illustrates amplitude values of the expansion coefficient corresponding to the various degrees, when the IQ signals illustrated in FIG. 5 are expanded by using the real-number polynomial function $R_m(t)$. As illustrated in FIG. 8, the amplitude corresponding to the second-degree coefficient 34 is too large.

In contrast, FIG. 9 illustrates amplitude values of the expansion coefficient, when the IQ signals illustrated in FIG. 5 are expanded by using the complex orthonormal basis $e_m(t)$ derived from the complex function $C_m(t)$ by performing the Schmidt orthogonalization. As illustrated in FIG. 9, the value corresponding to the second-degree coefficient 35 significantly decreases from the value corresponding to the first-degree coefficient, while the value corresponding to the third-degree coefficient 36 increases from the value corresponding to the second-degree coefficient. As explained herein, because the expansion coefficient switches from decreasing to increasing due to the incremental growth of the degree of expansion, it is possible to determine that the component up to the second-degree coefficient represents the clutter component and that the component corresponding to coefficients of the third-degree and higher represents the signal of the measurement target such as the blood. In contrast, in the example in FIG. 8, it is not possible to distinguish the clutter component from the signal of the measurement target, on the basis of the data.

Next, images generated by the ultrasound diagnosis apparatuses according to the conventional technique and the first embodiment will be compared with each other, with reference to FIGS. 10 and 11. FIG. 10 illustrates an example of an ultrasound diagnosis image according to the conventional technique. FIG. 11 illustrates an example of an ultrasound image generated by the ultrasound diagnosis apparatus according to the first embodiment. In FIGS. 10 and 11, the up-and-down direction corresponds to the depth direction, whereas the left-and-right direction corresponds to the azimuth direction.

In FIG. 10, the signal 40a is a blood flow signal at a smaller depth. The signal 42a is a blood flow signal at a larger depth. However, the noise 41a is noise occurring from an incomplete clutter elimination at the larger depth. According to the conventional technique, because the clutter elimination is incomplete, it is difficult to distinguish the signal 42a and the noise 41a from each other.

In contrast, in FIG. 11, the signal 40b is a blood flow signal at a smaller depth. The signal 42b is a blood flow signal at a larger depth. Further, because the level of precision of the clutter elimination is high in the region 41b, the noise is eliminated in the region 41b. As a result, the signal 42b is rendered while being separated from the clutter component.

As explained above, compared to the method that uses the real-number polynomial function, it is possible to improve the level of precision in the estimation and the suppression of the clutter, by using the complex orthonormal basis $e_m(t)$ derived from the complex function $C_m(t)$ by performing the Schmidt orthogonalization. Consequently, it is possible to improve the recognizability of the blood flow signal.

Possible embodiments are not limited to the examples described above. For instance, by employing the image generating function 154, the processing circuitry 150 may generate an ultrasound elastography image on the basis of the clutter component identified at step S145.

In this situation, elastography is to express in an image a distribution of levels of hardness of a tissue in a patient's body. Ultrasound elastography images are images obtained by implementing the procedure. Examples of ultrasound elastography can roughly be divided into two methods: One of the methods is a strain method by which the levels of hardness are visualized on the basis of magnitudes of strains on a scanned cross-sectional plane that are measured when an ultrasound probe is used to apply and release pressure to and from a tissue of a patient's body through the body surface. The other method is a shear wave method by which a modulus of elasticity is obtained by applying vibration to a tissue of a patient's body through the body surface with the use an acoustic radiation force or an external vibration source so as to cause a displacement and further measuring the displacement chronologically in each of various positions on a scanned cross-sectional plane so as to calculate a propagation velocity of a shear wave on the basis of the displacements.

In the following sections, an example with the strain method will be explained. However, the embodiment is also applicable to the shear wave method.

When the strain method is used, pressure is repeatedly applied and released to and from a tissue, as an operator manually oscillates the ultrasound probe 101. During that period of time, the ultrasound diagnosis apparatus according to the embodiment, for example, transmits the transmission waves at step S100 in FIG. 3 and subsequently receives the reflected waves at step S110, before performing the processes at steps S120 and S130. Within step S140, at steps S141 through S146, the ultrasound diagnosis apparatus according to the embodiment performs the same processes as described above.

When the processing circuitry 150 has calculated the clutter component at step S146 by employing the clutter component calculating function 152d, the processing circuitry 150 generates, as the motion information of the tissue that is a mobile member, tissue Doppler data obtained by extracting velocity values, dispersion values, and power values, with respect to multiple points within a two-dimensional space or a three-dimensional space. Subsequently, the processing circuitry 150 calculates strain distribution information indicating a spatial distribution of strains, from the generated tissue Doppler data. After that, the processing circuitry 150 generates an ultrasound elastography image by color-coding values of the strain distribution information, or the like, while employing the image generating function 154 (step S150) and causes the generated image to be displayed (step S160).

Possible embodiments are not limited to the example described above. For instance, an expression of the pre-orthogonalization function family A may be written as indicated in Expression (14) below, for example:

$$A=[C_0 e^{j\phi t}, C_1 e^{j\phi t}, C_2 e^{j\phi t}, C_3 e^{j\phi t}, \ldots, C_m e^{j\phi t}, \ldots]$$ (14)

In the present example, an expression of $C_m(t)$ may be written as indicated in Expression (15) below, for example:

$$C_m(t)=f^m$$ (15)

Further, in the present example, an expression of f(t) may be written as indicated in Expression (16) below, for example:

$$f(t)=t$$ (16)

In this situation, each of the expressions of the orthonormal basis $e_i(t)$ is obtained by multiplying an ordinary Legendre polynomial by a complex number having an absolute value of 1 and indicating a phase change in the clutter.

Further, in the embodiment above, the example is explained in which, with respect to the pre-orthogonalization function family A defined in the interval [−1, 1], the Hermitian inner product is defined with the application of the uniform weight under the $L_2$ norm so as to generate the orthonormal bases by performing the Schmidt orthogonalization on the basis of the defined inner product. However, possible embodiments of the defined inner product, the applied weights, and the interval in which the pre-orthogonalization function family A is defined are not limited to these examples. The method for introducing the inner product, the applied weights, and the interval in which the pre-orthogonalization function family A is defined may each be in any of a variety of forms. Accordingly, the plurality of functions (the orthonormal bases $e_i(t)$) that are generated therefrom may also be in any of a variety of forms.

Further, the generated plurality of functions may be a plurality of orthonormal bases generated by calculating direct products of the plurality of orthonormal bases, for example.

In other words, at the limit reached on the assumption that the second parameter φ is not present (φ=0), the generated plurality of mathematical functions (the orthonormal bases $e_i(t)$) may include, for example, a term corresponding to at least one selected from among the following: a Legendre polynomial, a Laguerre polynomial, a Chebyshev polynomial, a Hermite polynomial, a Bessel function, a spherical Bessel function, an associated Legendre polynomial, a spherical harmonic function, a Gegenbauer polynomial, and a Jacobi polynomial.

Further, in the embodiment above, the example is explained in which the plurality of functions represented by the orthonormal bases $e_i(t)$ are generated by performing the Schmidt orthogonalization on the pre-orthogonalization function family A; however, possible embodiments are not limited to this example. For instance, the generated plurality of functions do not necessarily have to be normal and do not necessarily have to be bases that are orthogonal. For example, an expansion operation using unstandardized orthogonal bases is an operation substantially equivalent to an expansion operation using the orthonormal bases. Further, when the bases subject to an expansion process are at least linearly independent of each other, it is possible to uniquely determine the expansion coefficient for these bases, with respect to the given time-series data. Accordingly, the processing circuitry 150 may calculate an expansion coefficient, by using bases that are linearly independent of each other and are not orthogonal to each other.

For example, the processing circuitry 150 may generate a plurality of functions by performing an identity transformation process on the pre-orthogonalization function family A (which means that the plurality of functions are elements themselves of the pre-orthogonalization function family A) so as to calculate an expansion coefficient by using the plurality of functions as bases.

Further, in view of the purpose of eliminating (suppressing) the clutter component, not all of the bases subject to the expansion process have to be linearly independent of each other. For example, as long as the dimension of the linear space structured by the bases subject to the expansion process is two or more, the processing circuitry 150 may calculate an expansion coefficient by causing certain bases a part of which are linearly dependent on each other to be subject to the expansion process, so as to calculate a clutter component by using the calculated expansion coefficient. In that situation, as long as the bases identified as a clutter component are linearly independent of each other, the processing circuitry 150 is able to uniquely determine the value of the clutter component, regardless of the fact that it is not possible to uniquely determine the expansion coefficient.

Second Embodiment

In a second embodiment, an example will be explained in which a process is performed by calculating the second parameter ϕ from the time-series data itself. More specifically, on the basis of the parameter value obtaining function 152a, the processing circuitry 150 calculates a value of the second parameter ϕ on the basis of the IQ signals (the time-series data) generated at step S130 in FIG. 3. On the basis of a result calculated based on the parameter value obtaining function 152a described above, the processing circuitry 150 generates the abovementioned expansion coefficient.

At steps S100 through S130 and steps S150 through S170 illustrated in FIG. 3, an ultrasound diagnosis apparatus according to the second embodiment performs the same processes as those performed by the ultrasound diagnosis apparatus according to the first embodiment. Further, also at step S140 in FIG. 3, the ultrasound diagnosis apparatus according to the second embodiment performs the same processes as those performed by the ultrasound diagnosis apparatus according to the first embodiment at steps S142 through S147, excluding step S141 in FIG. 4. Accordingly, explanations of the processes other than the process at step S141 will be omitted.

Figure 12:
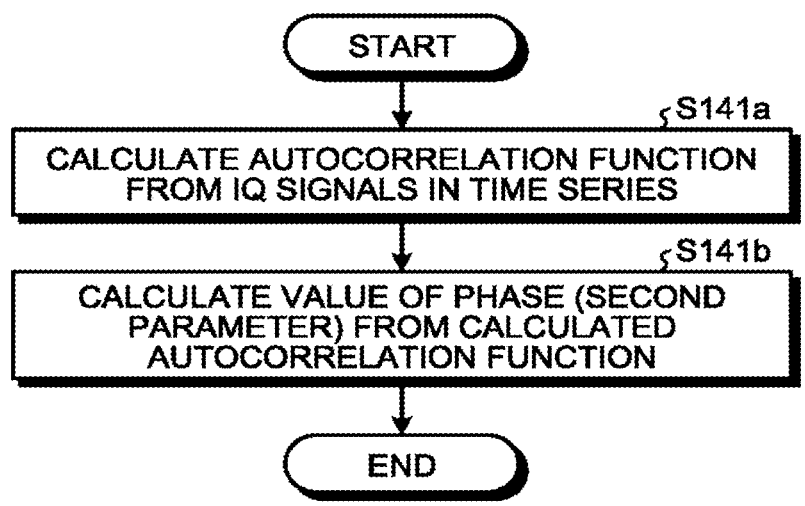
FIG. 12 is a flowchart for explaining a flow in a process performed by an ultrasound diagnosis apparatus according to a second embodiment.

FIG. 12 is a chart for explaining a flow in a process performed by the ultrasound diagnosis apparatus according to the second embodiment. More specifically, FIG. 12 is a chart for more specifically explaining the process performed at step S141 in FIG. 4 by the ultrasound diagnosis apparatus according to the second embodiment.

By employing the parameter value obtaining function 152a, the processing circuitry 150 calculates an autocorrelation function from the IQ signals in a time series (the time-series data) (step S141a). Subsequently, by employing the parameter value obtaining function 152a, the processing circuitry 150 calculates a value of the phase (the second parameter ϕ) from the calculated autocorrelation function (step S141b). In other words, by employing the parameter value obtaining function 152a, the processing circuitry 150 calculates the value of the second parameter ϕ, on the basis of the autocorrelation function calculated at step S141a.

More specifically, the processing circuitry 150 calculates a phase of the autocorrelation function calculated from IQ signals of which the quantity is equal to N (where 2≤N≤K) selected from among as many IQ signals as K that are the time-series IQ signals. In this situation, the phase of the autocorrelation function can be expressed as indicated in Expression (17) below, when the I signals of which the quantity is equal to N are expressed as $I(t_1), \ldots,$ and $I(t_n)$, whereas the Q signals of which the quantity is equal to N are expressed as $Q(t_1), \ldots,$ and $Q(t_n)$.

$$\phi = \arctan\left(\frac{\sum_{K=1}^{N-1}\{I(t_{K+1})Q(t_K) - Q(t_{K+1})I(t_K)\}}{\sum_{K=1}^{N-1}\{I(t_{K+1})I(t_K) - Q(t_{K+1})Q(t_K)\}}\right) \quad (17)$$

In the manner described above, by performing the processes at steps S141a and S141b, the ultrasound diagnosis apparatus according to the second embodiment performs the process at step S141 in FIG. 4. Subsequently, the ultrasound diagnosis apparatus according to the second embodiment performs the processes at step S142 and thereafter.

Possible embodiments are not limited to the example described above. For instance, at step S141a, the ultrasound diagnosis apparatus according to the second embodiment may calculate the second parameter ϕ on the basis of at least one of an average value of phase differences among data, a median value of phase differences among data and a representative value selected from phase differences among data, the data being calculated from the IQ signals of which the quantity is equal to N (where 2≤N≤K) selected from among as many IQ signals as K that are the time-series IQ signals. Further, the second embodiment may be combined with any of the various elements described in the first embodiment as appropriate. For example, the processes according to the second embodiment may be combined with the processes described in the first embodiment and used for generating an ultrasound elastography image.

As explained above, the ultrasound diagnosis apparatus according to the second embodiment is configured to calculate the phase information (the second parameter ϕ) from the measured packet. It is therefore possible to save the trouble of the user giving the second parameter ϕ. Further, even when the second parameter ϕ is different for each of various locations, for example, it is possible to automatically calculate the second parameter ϕ.

Third Embodiment

In a third embodiment, an example in which a clutter has a plurality of components will be explained.

When a clutter has a plurality of components, for example, it is possible to adopt a function system as indicated in Expression (18) below, as an expression of f(t) in Expression (3).

$$f = t\sum_i \lambda_i e^{j\phi_i t} \quad (18)$$

In Expression (18), the symbol "$\phi_i$" is a parameter expressing a phase change in an i-th component of the clutter. The symbol "$\lambda_i$" is a parameter expressing a weight applied to the i-th component of the clutter. For example, when the clutter has two components, the expression of f(t) can be written as indicated in Expression (19) below:

$$f = t[\lambda_1 e^{j\phi_1 t} + \lambda_2 e^{j\phi_2 t}] \quad (19)$$

In Expression (19), the symbols "$\phi_1$" and "$\phi_2$" denote parameters expressing the phase change in a first component and the phase change in a second component of the clutter, respectively. The symbols "$\lambda_1$" and "$\lambda_2$" denote parameters expressing a weight applied to the first component of the clutter and a weight applied to the second component of the clutter, respectively. In other words, the pre-orthogonalization function family A has the first parameter t, the second parameter $\phi_1$, and the third parameter $\phi_2$ that is different from the first parameter t and the second parameter $\phi_1$, as arguments. In the present example, the second parameter $\phi_1$ is a parameter expressing the phase change in the first component of the clutter. The third parameter $\phi_2$ is a parameter expressing the phase change in the second component of the clutter.

When Expression (19) is substituted to Expression (3), a specific expression of the pre-orthogonalization function family A can be written as indicated in Expression (20) below:

$$A = [1, t(\lambda_1 e^{j\phi_1 t} + \lambda_2 e^{j\phi_2 t}), t^2(\lambda_1^2 e^{j(2\phi_1)t} + 2\lambda_1\lambda_2 e^{j(\phi_1+\phi_2)t} + \lambda_2^2 e^{j(2\phi_2)t}), \ldots] \quad (20)$$

The processing circuitry 150 performs the same processes as those in the first embodiment on the pre-orthogonalization function family A.

Processes performed by an ultrasound diagnosis apparatus according to the third embodiment will be explained, with reference to, again, the flowcharts in FIGS. 3 and 4. At steps S100 through S130 and steps S150 through S170 in FIG. 3, the ultrasound diagnosis apparatus according to the third embodiment performs the same processes as those performed by the ultrasound diagnosis apparatus according to the first embodiment. Further, also at step S140 in FIG. 3, the ultrasound diagnosis apparatus according to the third embodiment performs the same processes as those performed by the ultrasound diagnosis apparatus according to the first embodiment at steps S143 through S147, excluding steps S141 and S142 in FIG. 4. Accordingly, detailed explanations of the same processes will be omitted. In the following sections, an example in which the clutter has as many components as L, where L is a natural number of 2 or larger (Expression (18)) will be explained.

By employing the parameter value obtaining function 152*a*, the processing circuitry 150 according to the third embodiment obtains values of parameters $\phi_1, \phi_2, \phi_3, \ldots$ and $\phi_L$ that are different from the first parameter t related to time, in a process corresponding to step S141 according to the first embodiment. In addition, by employing the parameter value obtaining function 152*a*, the processing circuitry 150 obtains values of parameters $\lambda_1, \lambda_2, \lambda_3$, and $\lambda_L$.

As for a method for obtaining these parameters, the processing circuitry 150 may obtain these parameters from the user via the input circuitry 134. In another example, the processing circuitry 150 may obtain these parameters by repeatedly performing the same processes as those performed in the second embodiment.

On the basis of the obtained parameters, the processing circuitry 150 generates the pre-orthogonalization function family A, by using Expression (18), for example (step S142). Subsequently, the processing circuitry 150 generates the orthogonal bases $e_i(t)$ by performing an orthogonalization process according to a predetermined method (step S143). After that, the processing circuitry 150 calculates an expansion coefficient by expanding the time-series data of the IQ signals while using the generated orthogonal bases $e_i(t)$ (step S144). The processing circuitry 150 then eliminates the clutter component by performing the processes at steps S145 through S147.

By using the ultrasound diagnosis apparatus according to the third embodiment, it is possible to efficiently eliminate the clutter having the plurality of components.

Computer Programs

It is possible to execute instructions indicated in the processing procedures described in any of the embodiments described above, on the basis of a computer program (hereinafter, "program") represented by software. When a general-purpose computer system stores the program therein in advance, it is possible to achieve the same advantageous effects as those achieved by the ultrasound diagnosis apparatuses and the signal processing apparatuses (the image processing apparatuses) according to the embodiments described above, by reading the stored program. The instructions described in the embodiments above are recorded as a computer-executable program on a magnetic disk (a flexible disk, a hard disk, or the like), an optical disk (a Compact Disk Read-Only Memory (CD-ROM), a Compact Disk Recordable (CD-R), a Compact Disk Rewritable (CD-RW), a Digital Versatile Disk Read-Only Memory (DVD-ROM), a DVD recordable (DVD±R), a DVD Rewritable (DVD±RW), or the like), a semiconductor memory, or any other similar recording media. Any storage format may be used as long as a computer or an incorporated system is able to read data from the storage medium. The computer is able to realize the same operations as those performed by the ultrasound diagnosis apparatuses and the signal processing apparatuses (the image processing apparatuses) according to the embodiments described above, by reading the program from the recording medium and causing a CPU to execute the instructions written in the program on the basis of the read program. Needless to say, when the computer obtains or reads the program, the computer may obtain or read the program via a network.

Further, on the basis of the instructions of the program installed from the storage medium into a computer or an incorporated system, an Operating System (OS) working in the computer, database management software, or middleware (MW) used in a network or the like may execute a part of the processes for realizing any of the embodiments described above.

Furthermore, the storage medium does not necessarily have to be a medium independent of the computer or the incorporated system. Examples of the storage medium include a storage medium that downloads and stores therein or temporarily store therein the program transmitted via a Local Area Network (LAN) or the Internet.

Further, the storage medium does not necessarily have to be singular. Examples of the storage medium according to the embodiments include the situation where the processes of any of the embodiments described above are executed from two or more media. The medium or the media may have any configuration.

The computer or the incorporated system according to any of the embodiments is configured to execute the processes in the embodiment on the basis of the program stored in the storage medium and may be configured in any of various forms including the following: a single apparatus such as a personal computer or a microcomputer; and a system or the like in which a plurality of apparatuses are connected via a network.

Further, the term "computer" according to the embodiments does not necessarily have to be a personal computer and may be an arithmetic processing unit included in an information processing device, a microcomputer, or the like. The term "computer" generally refers to any device or apparatus that is capable of realizing the functions described in the embodiments by using one or more programs.

Figure 13:
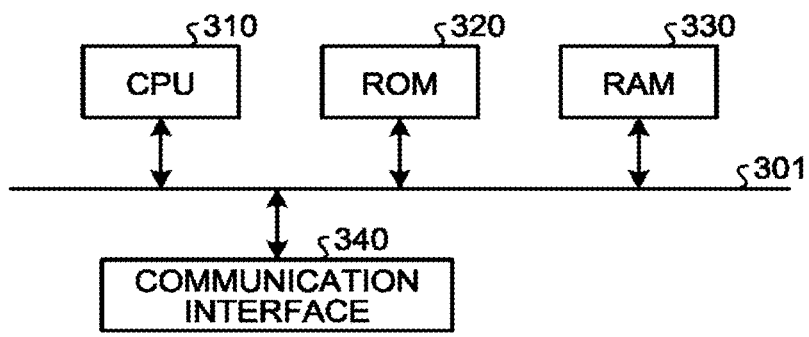
FIG. 13 is a diagram for explaining a hardware configuration of a signal processing apparatus according to an embodiment.

FIG. 13 is a diagram illustrating a hardware configuration of the processing circuitry 150 (the signal processing apparatus) according to the embodiments. The signal processing apparatus (the image processing apparatus) according to the embodiments described above includes a controlling device such as a Central Processing Unit (CPU) 310, storage devices such as a Read-Only Memory (ROM) 320, a Random Access Memory (RAM) 330 and/or the like, a communication interface 340 that performs communication by making a connection to a network, and a bus 301 that connects the functional units to one another.

The program executed by the image processing apparatus according to the embodiments described above is provided as being incorporated in advance in the ROM 320 or the like. Further, the program executed by the signal processing apparatus (the image processing apparatus) according to the embodiments described above is able to cause a computer to function as the functional units of the signal processing apparatus (the image processing apparatus) described above. The computer is configured so that the CPU 310 is capable of reading the program from a computer-readable storage medium into a main storage device and executing the read program.

By using the ultrasound diagnosis apparatus according to at least one aspect of the embodiments described above, it is possible to efficiently eliminate the clutter.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound apparatus comprising:
   an ultrasound probe configured to transmit an ultrasound wave to a patient and to receive a reflected wave of the ultrasound wave; and
   processing circuitry configured to obtain time-series data having complex values based on the reflected wave of the ultrasound wave transmitted by the ultrasound probe, configured to calculate an expansion coefficient in a case in which the obtained time-series data is expressed as a linear sum of a plurality of mathematical functions, the time-series data having, as an argument, a first parameter related to time, configured to identify a clutter component included in the time-series data, based on the expansion coefficient, and configured to generate an image from a signal component obtained by subtracting the clutter component from the time-series data,
   wherein the plurality of mathematical functions are mathematical functions that are generated by implementing an orthogonalization method on a pre-orthogonalization function family that has, as arguments, the first parameter and a second parameter different from the first parameter, and
   the reflected wave of the ultrasound wave comprises a wave reflected off either (1) a blood flow in the patient or (2) a moving cardiac wall in the patient.

2. The ultrasound apparatus according to claim 1, wherein the second parameter is a parameter calculated based on a phase change of a clutter.

3. The ultrasound apparatus according to claim 1, wherein the plurality of mathematical functions are the mathematical functions having values in complex numbers.

4. The ultrasound apparatus according to claim 1, wherein the processing circuitry is configured to identify a degree of expansion at which the expansion coefficient switches from decreasing to increasing as the degree of expansion increases and further configured to identify the clutter component based on the identified degree of expansion at which the expansion coefficient switches from decreasing to increasing.

5. The ultrasound apparatus according to claim 1, wherein the processing circuitry is configured to identify a component corresponding to one or more degrees of expansion equal to or lower than a predetermined degree of expansion as the clutter component.

6. The ultrasound apparatus according to claim 1, wherein the processing circuitry is configured to generate an ultrasound elastography image based on the identified clutter component.

7. The ultrasound apparatus according to claim 1, further comprising: input circuitry configured to receive an input of a value of the second parameter from a user, wherein the processing circuitry is configured to calculate the expansion coefficient based on a result of the input received by the input circuitry.

8. The ultrasound apparatus according to claim 1, wherein the processing circuitry is configured to calculate a value of the second parameter based on the time-series data and further configured to generate the expansion coefficient based on the calculated value of the second parameter.

9. The ultrasound apparatus according to claim 8, wherein the processing circuitry is configured to calculate an autocorrelation function from the time-series data and further calculates the value of the second parameter based on the calculated autocorrelation function.

10. The ultrasound apparatus according to claim 8, wherein the processing circuitry is configured to calculate, from the time-series data, the value of the second parameter based on at least one of an average value of phase differences among some of the time-series data, a median value of phase differences among some of the time-series data and a representative value selected from phase differences among some of the time-series data.

11. The ultrasound apparatus according to claim 1, wherein, at a limit reached on an assumption that the second parameter is not present, the plurality of mathematical functions include a term corresponding to at least one selected from among: a Legendre polynomial, a Laguerre polynomial, a Chebyshev polynomial, a Heiinite polynomial, a Bessel function, a spherical Bessel function, an associated Legendre polynomial, a spherical haimonic function, a Gegenbauer polynomial, and a Jacobi polynomial.

12. The ultrasound apparatus according to claim 1, wherein
   the pre-orthogonalization function family further has a third parameter as an argument, the third parameter being different from the first parameter and the second parameter,
   the second parameter is a parameter expressing a phase change in a first component of a clutter, and
   the third parameter is a parameter expressing a phase change in a second component of the clutter.

13. An ultrasound wave processing method comprising:
   using an ultrasound probe to transmit an ultrasound wave to a patient
   obtaining, by processing circuitry, time-series data having complex values based on a reflected wave of the ultrasound wave transmitted by the ultrasound probe, the time-series data having, as an argument, a first parameter related to time;
   calculating, by the processing circuitry, an expansion coefficient in a case in which the time-series data is expressed as a linear sum of a plurality of mathematical functions, and identifying, by the processing circuitry, a clutter component included in the time-series data, based on the expansion coefficient; and
   generating, by the processing circuitry, an image from a signal component obtained by subtracting the clutter component from the time-series data,
   wherein the plurality of mathematical functions are mathematical functions that are possible to be generated by implementing an orthogonalization method on a pre-orthogonalization function family that has, as arguments, the first parameter and a second parameter different from the first parameter, and
   the reflected wave of the ultrasound wave comprises a wave reflected off either (1) a blood flow in a patient or (2) a moving cardiac wall in the patient.

14. The ultrasound apparatus according to claim 1, wherein the orthogonalization method comprises a Schmidt-orthogonalization method on the pre-orthogonalization function family.

15. The signal processing method according to claim 13, wherein the orthogonalization method comprises a Schmidt-orthogonalization method on the pre-orthogonalization function family.

16. The ultrasound apparatus according to claim 1, wherein the reflected wave of the ultrasound wave is a wave reflected off of a blood flow in the patient.

17. The ultrasound apparatus according to claim 1, wherein the reflected wave of the ultrasound wave is a wave reflected off of a moving cardiac wall in the patient.

* * * * *